United States Patent
Yadlapalli et al.

(10) Patent No.: US 11,896,709 B2
(45) Date of Patent: Feb. 13, 2024

(54) NATURAL VEGETABLE SOURCE BASED HAIR COLOUR

(71) Applicant: GODREJ CONSUMER PRODUCTS LTD., Mumbai (IN)

(72) Inventors: Venkateswara Yadlapalli, Mumbai (IN); Adrija Jha, Mumbai (IN); John Naik, Mumbai (IN); Manoj Gaur, Mumbai (IN); Reena Bibals, Mumbai (IN); Rajan Raghavachari, Mumbai (IN); Rupinder Rawat, Mumbai (IN)

(73) Assignee: GODREJ CONSUMER PRODUCTS LTD., Mumbai (IN)

( * ) Notice: Subject to any disclaimer, the term of this patent is extended or adjusted under 35 U.S.C. 154(b) by 0 days.

(21) Appl. No.: 18/173,971

(22) Filed: Feb. 24, 2023

(65) Prior Publication Data

US 2023/0270662 A1    Aug. 31, 2023

(51) Int. Cl.
  *A61Q 5/10*    (2006.01)
  *A61K 8/9789*    (2017.01)
  *A61K 8/19*    (2006.01)
  *A61Q 5/06*    (2006.01)

(52) U.S. Cl.
  CPC .............. *A61K 8/9789* (2017.08); *A61K 8/19* (2013.01); *A61Q 5/065* (2013.01); *A61Q 5/10* (2013.01); *A61K 2800/42* (2013.01); *A61K 2800/48* (2013.01)

(58) Field of Classification Search
  CPC .... A61K 8/9789; A61K 8/19; A61K 2800/42; A61K 2800/48; A61Q 5/065; A61Q 5/10
  USPC .......................................................... 8/405
  See application file for complete search history.

(56) References Cited

U.S. PATENT DOCUMENTS

| | | | |
|---|---|---|---|
| 4,004,877 A | 1/1977 | Saphir | |
| 4,801,302 A | 1/1989 | Grollier | |
| 5,725,602 A | 3/1998 | Belcour-Castro | |
| 7,550,014 B2 * | 6/2009 | Greaves | A61K 8/9789 8/405 |
| 8,029,576 B2 * | 10/2011 | Noecker | A61Q 5/065 8/405 |
| 8,795,391 B2 * | 8/2014 | Iizaki | A61K 8/416 8/606 |
| 2003/0066140 A1 | 4/2003 | Bartolone | |
| 2005/0257331 A1 * | 11/2005 | Nocker | A61Q 5/10 8/405 |

(Continued)

FOREIGN PATENT DOCUMENTS

| | | | | |
|---|---|---|---|---|
| EP | 2417965 A1 * | 2/2012 | | A61Q 5/10 |
| EP | 3037485 A1 * | 6/2016 | | A61Q 5/065 |

(Continued)

OTHER PUBLICATIONS

Ochiai et al., J. Cosmetic. Sci. 56: 29-46, 2005.

*Primary Examiner* — Eisa B Elhilo
(74) *Attorney, Agent, or Firm* — Kramer & Amado P.C.

(57) ABSTRACT

The present invention describes a novel natural hair colour composition containing (a) a mixture of basic salt which aid in opening the hair cuticle and facilitating better penetration of dye which is natural plant-based extract; (b) a metal salt based mordanting agent which form a dye-metal complex. The invention further describes 2 step method of application which give better penetration and hence improved colour delivery and wash off resistance.

17 Claims, 1 Drawing Sheet a    b    c

(56) References Cited

U.S. PATENT DOCUMENTS

2009/0249563 A1* 10/2009 Greaves .............. A61K 8/9789
8/405
2017/0027832 A1* 2/2017 Wang .................. A61K 8/8147
2018/0340107 A1* 11/2018 Nöcker ................. C08G 75/08

FOREIGN PATENT DOCUMENTS

WO      2007130777 A2    11/2007
WO   WO 2012127502 A1 *  9/2012  ............ A61Q 5/065

* cited by examiner

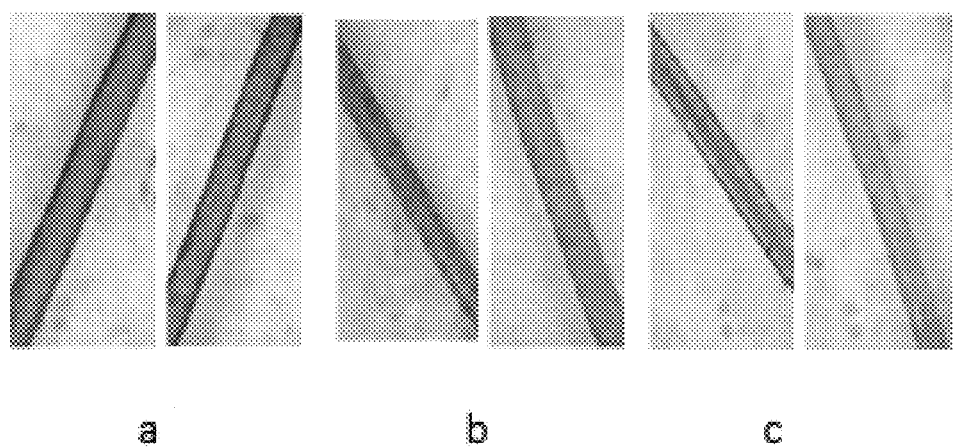
a　　　　　　b　　　　　　c

NATURAL VEGETABLE SOURCE BASED HAIR COLOUR

FIELD OF INVENTION

The invention is in field of natural colours for keratinous fibres, specifically hair. More particularly, the present invention relates to natural colours obtained from Brazilin family and method for application thereof.

BACKGROUND OF INVENTION

Oxidative hair colours have been used for hair colouration since ages. Said oxidative hair colours consists of ortho- or para-phenylenediamines, ortho/para aminophenols and heterocyclic compounds. These substances are colourless by themselves, but give dark, elegant coloration when used with appropriate oxidising agent. It has also been known to dye hair fibres with dyeing compositions containing direct dyes. These dyes can be non-ionic, anionic, cationic or amphoteric with affinity for hair fibres. Hair dyes can be made of synthetic origin dyes of natural based extracts and/or dyes.

There has been a gradual awareness regarding the harmful effects of the chemical dyes and the hazardous nature of these dyes for hair. Further, many of these chemicals have been assessed to have carcinogenic effects. Hence, there is an increasing demand of natural product based, non-toxic hair dyes which have low toxicity and are environment friendly. The natural dyes have attracted attention all over the globe.

The colouring of hair, especially living human hair, with the help of natural dyes, has been known since ancient times, henna in particular, however, this knowledge has been pushed into the background for years in favour of synthetic dyes that are more reproducible and easier to produce.

Natural Vegetable based hair colouring product composition containing henna & indigo extracts are bulky, time consuming and inconvenient in application, Over past few years there have been number of attempts by various inventors to develop variety of dyes which are based on naturally obtained colours.

For instance, U.S. Pat. No. 7,550,014 and WO 2007130777 by Greaves et al., teaches a composition for dyeing keratin fibres, comprising approximately 0.1 to 30 percent of at least one concentrated plant dye extracted using at least one of a solvent extraction process and a supercritical $CO_2$ extraction process, and a mineral or metallic salt with approximately 0.01 to 5 percent active metal capable of acting as a mordanting agent, and wherein at least one of the concentrated plant dye and the mineral or metal salt capable of acting as a mordanting agent is encapsulated in a water impermeable shell. The crux of this prior art is mainly based on the attainment of substantially pure plant dyes by solvent or supercritical $CO_2$ extraction, and mordanting with mineral or metallic salts in combination with or without encapsulation, to create safe hair dyes that unexpectedly and surprisingly produce bright and permanent or semi-permanent colours similar to synthetic dyes in 10-20 minutes or less, thereby improving on the safety, durability, quality and application time of existing products on the market.

The said dyes and mineral salts are packaged separately in aqueous solutions and are mixed together just before use. The metals act as a mordant which helps to hold the dyes on the hair to provide for a permanent colouring effect against shampooing. The colour solution contains citric acid and lactic acid whereby the final colouring solution is at quite low pH values which can be hazardous to hair.

US2009/0249563 also by Greaves et al., teaches a composition for dyeing keratin fibres, comprising approximately 0.1 to 30 percent of at least one concentrated plant dye and a mineral or metallic salt with approximately 0.01 to 5 percent active metal capable of acting as a mordanting agent, wherein the mineral or metallic salt is selected from the group consisting of iron gluconate, ferrous aspartate, copper gluconate, calcium gluconate, calcium aspartate, sodium gluconate, magnesium gluconate, magnesium aspartate, magnesium citrate, magnesium palmitate, zinc gluconate, zinc aspartate, and manganese gluconate, which are essentially organic acid based mordanting agents.

U.S. Pat. No. 4,801,302, by Grollier et al., discloses a process for dyeing hair in several separate steps consisting in applying a cosmetically acceptable composition containing at least one cupric salt and, before or after this application, a cosmetically acceptable composition containing a dye chosen from brazilin and its hydroxyl derivative wherein the copper content in the composition containing said cupric salt is between 0.01 and 2% by weight, and said dye is present in the composition containing it in a proportion between 0.05 and 5% by weight. The cupric salt is selected from Cupric-chloride, sulphate, nitrate, acetate which was used in combination with Haematoxylin dye and/or Brazilin dye to give different colour shades under different pH conditions adjusted by external source of alkali/acids.

U.S. Pat. No. 4,004,877 by Saphir et al teaches about aerial oxidation of natural and synthetic hair comprising of an air oxidation hair dye, a metal complex compound and a solvent which keeps the air oxidation hair dye and the metal complex compound in solution. Said metal complex compound consists of a metal, present in a quantity ranging from 0.1% to less than 1% by weight and selected from the group consisting of copper, iron, manganese, cobalt, nickel, chromium, titanium, tin, hafnium, zinc, vanadium, zirconium and molybdenum; a complex forming agent, present in the weight percent range corresponding to that of said metal quantity given above, and monoethanolamine ranging from 1.0% to 1.36% by weight, said solvent, ranging from 38.3% to 55.25% by weight. Said solvent comprises formamide. The copper metal in the said air oxidation hair dye is present in the form of copper sulphate, said complex forming agent is tartaric acid, and wherein said solvent includes isopropyl alcohol and formamide. The aforesaid cited art involves an amine and a complexing agent such as tartaric acid in its air oxidation hair dye formulation.

US20030066140 by Bartolone et al.: is directed to a composition for coloring hair which comprises a first composition comprising: (a) a dye forming transition metal salt or complex; and a second composition which comprises the following two compositions which are mixed just prior to application to the hair: (a) a composition comprising a water-soluble peroxygen oxidizing agent; and (b) a composition comprising one or more oxidative hair coloring agents selected from the group consisting of an aromatic diamine, an aminophenol, a polyhydric phenol a catechol and mixtures thereof. The aforesaid prior art involves the use of a water-soluble peroxygen oxidizing agent in its hair colouring composition Regarding Natural hair dyeing agent prepared by plant pigment catechu and hair dyeing method by Hou et al., the same teaches a hair dying agent comprising two parts, agent A and agent B. Agent A comprises with: 1. (by wt %) 3-10% of plant color matter catechu, a traditional Chinese medicinal material. 2. 10-50% of organic solvent. 3. Water Agent B comprises with; 1. (by wt %) 1-5% of ferrous salt mordant. 2. 0.2-1.0% of reduced iron powder. 3. 1-10% of surfactant. 4. 1-5% of thickening agent. 5. Acidifying agent. 6. 0.1-0.3% of natural essence. 7. Water This prior art involves acidifying agent in its composition.

U.S. Pat. No. 5,725,602 by Balcour Carbo et al., is directed to a hair dyeing process comprising the steps of: a) obtaining a composition in the form of an aqueous dispersion containing a product of grinding plants or parts of plants of the species *Impatiens balsamina*, in an appropriate liquid carrier, said dispersion forming a pulp which has a consistency that is sufficient to coat the hair and to adhere thereto without running after the application to the hair; b) bringing the hair to be dyed into contact with the composition as obtained in a) above; c) and maintaining the said contact for a sufficient period to obtain the desired colour. The above prior art does not involve any mordanting agent.

Regarding a novel permanent acid type hair color mode possible with dye metal ion technology in J. Cosmetic. Sci. 56: 29-46, 2005 by Ochiai et al, the same is based on the interaction of various metal ions namely $AlCl_3 \cdot 6H_2O$, $ZnCl_2$, $FeCl_2 \cdot 4H_2O$, $MnCl_2 \cdot 4H_2O$, $NaCl$, $KCl$, $MgCl_2 \cdot 6H_2O$, $CuSO_4 \cdot 5H_2O$, $FeSO_4 \cdot 7H_2O$ and $BaCl_2 \cdot 2H_2O$, in permanent hair dyes. Specifically, the superior efficacy of $AlCl_3 \cdot 6H_2O$ (optimum concentration 0-1.6%) in dye uptake is disclosed and the contribution of the acidic compounds such as formic acid, lactic acid, acetic acid, glycine hydrochloride, tretronic acid and specifically glycolic acid (concentration 0-3.2% in colour brightness and in long retention of the colour is also taught and optimum concentration of 1.6% was determined.

In spite of good amount of literature on plant-based hair dyes, there are certain areas of concern such as wash off resistance, photo stability, and coverage. Further, due to large size of natural pigments plant-based hair dyes have limitation of colour delivering capability such as low intensity, dull shades, apart from reproducibility issues and they are expensive as compared to synthetic hair dyes.

SUMMARY OF THE INVENTION

According to the concept of the present invention, at least one or more inorganic/organic basic salts is employed to open/well cuticle and facilitate the further procedure. Traditionally, quick acting bases like ammonia, guanidine salts, Monoethanolamine, triethanolamine, urea, thio-substituted compounds are being used to promote entry of monomers into the hair which have ill effect on hairs. The composition involves use of an inorganic base such as alkali metal carbonate/bicarbonate/oxide/hydroxide which swells/opens hair cuticle for maximum penetration of the natural dyes. The core issue of inability of the natural colouring pigments to penetrate the shaft or exocuticle of hair, is addressed leading to development of natural hair colour which gives uniform coverage with better penetration and wash off resistance and is expected to give good root coverage on human hair. The natural ingredients in the mixture also ensures photo-protection.

Dyes used in this process include, but not limited to, polyhydroxy dyes like oxidised and non-oxidised logwood extract that oxidise to reactive intermediates which in turn give dark colouration with various shades in the presence of mordant.

The other part of this invention involves bivalent and multivalent inorganic metal salts resulting in strong co-ordination bonds with certain dyes giving dark and long-lasting colour.

The process can be carried out with subsequent applications without washing and the expected colouration is achieved at ambient conditions. The obtained colour matures over time to progress getting even darker as the co-ordination of dye metal complex strengthens. Additionally, the non-oxidized form of logwood extract also contributes to the darkening effect over time post washing of hair due to its air oxidation.

According to another preferred aspect of the present invention, there is provided a hair colour composition comprising:

Part A:
 a) at least one or more inorganic/organic base salts which provides optimum pH to facilitate opening of cuticle and
 b) at least one or more dye, vegetable dye, concentrated plant dye containing;
  i) suitable hair grooming/ benefiting agent;
  ii) penetration aiding agent comprising anyone or more of organic acids such as lactic acid, glycolic acid, citric acid; organic ethers, alcohols such as ethanol, isopropyl alcohol, butyl alcohol, isobutyl alcohol, benzyl alcohol, and aldehydes, and oxones;

Part B
at least one or more inorganic metal salt based mordanting agent selected from anyone or more of:
 i) copper salts, ferrous salts, chrome salts, tin salts, potassium salts, Zinc salts, Aluminium slats or combination thereof.

It is thus a path breaking strategy based on utilization of at least one or more base/swelling agent in combination with at least one or more vegetable dye/concentrated plant dye, followed by post-mordanting involving,—at least one or more inorganic metal salt based mordanting agent for generating dye/plant dye/concentrated plant dye-metal complex free of oxidizing agents and chemical additives, providing dark colours with superior colour delivery and better wash-off resistance at ambient conditions.

BRIEF DESCRIPTION OF DRAWINGS

FIG. 1 illustrates post-mordanting wash-out studies.

DETAILED DESCRIPTION OF DRAWINGS

FIG. 1 show micrographs of hair strand showing initial colour and colour retention after 10 washes (micrographs b) and after 20 washes (micrographs c). as can be deciphered from the micrographs, the hair dyed with natural colour composition of invention show an excellent wash resistance, at least upto 20 washes.

DETAILED DESCRIPTION OF INVENTION

The invention will now be described in detail in connection with certain preferred and optional embodiments, so that various aspects thereof may be more fully understood and appreciated. As used herein, the following terms and phrases shall have the meaning set forth below.

Unless specified otherwise, all technical and scientific terms used herein have the same meaning as commonly understood by one of ordinary skill in the art, to which this invention belongs. Although any methods and materials similar or equivalent to those described herein can be used in the practice or testing of the present invention, the preferred methods and materials are described. To describe the invention, certain terms are defined herein specifically as follows.

Unless stated to the contrary, any of the words "contains", "containing", "including," "includes," "comprising," and "comprises" mean "including without limitation" and shall not be construed to limit any general statement that it follows to the specific or similar items or matters immediately following it. Embodiments of the invention are not mutually exclusive, but may be implemented in various combinations. The described embodiments of the invention and the disclosed examples are given for the purpose of illustration rather than limitation of the invention as set forth in the appended claims.

Further, words like "a", "an", "at least" and "the" should be construed to not only cover singular quantities but also plural quantities of the elements immediately following them.

For the purpose of this specification the term "Dye" also encompasses a dye or a vegetable dye or a concentrated plant extract with other ingredients responsible for hair texture improvements.

The present invention describes a hair colour composition for dyeing keratin fibres comprising a inorganic basic salt having an ability to aid in opening of hair cuticle by providing optimum pH and dye/plant extract along with other ingredients for hair texture improvements and an inorganic metal salt based mordanting agent for generating dye-metal complex free of oxidizing agents, with uniform and superior colour delivery and colour variance under ambient temperature conditions.

In an embodiment, the present invention provides a hair colour composition containing (a) a basic salt in amount to 0.5% to 8% by weight and one or more dye present in combined amounts of 0.1% to 20% by weight along with other ingredients for hair texture improvements (b) an inorganic metal salt based mordanting agent present in amounts of 0.01% to 10% by weight of the active metal in the composition.

Accordingly, the inorganic metal salt aid in opening of cuticle which facilitates penetration of large dye molecules. The pH range at which this happens does not cause damage to keratin fibres as compared to the traditional bases such as ammonia and related compounds.

In accordance with the above embodiments, the cuticle opening basic salt is an organic base or inorganic base selected from oxides, carbonates, silicates, bicarbonates and carboxyl amine compounds.

Further, in accordance with the above embodiments, the dye is either a pure dye or an extract or concentrate of the plant material or an unprocessed plant material that selectively includes flavonoids, terpenoids, polyphenolics or its derivatives as the basic molecular skeleton including selective additional mono-azo, hydroxyl, carboxyl or amino groups and preferably comprises anthocyanins preferably non-oxidised logwood extract and oxidised logwood extract, tanins, Benzoquinones, naphthoquinones preferably Henna, Walnut, anthroquinones preferably Alizarin, carotenoids, indigo, indigocaramine, rubiethyric acid, purpuroxanthin, rubiadin, morindanigrin, munjistin, morindadiol, carotene, crocentin, bixin, canthaxanthin, lycopene, capsanthin, apocarotenal, xanthophyll, curcumin, morin, malclurin, luteolin, apigenin, fukugetin, datiscetin, kaempferol, rhamnocitrin, rhamnethin, zanthorhamnin, isorhamnetin, rharmazin, quercetin, rutin, gossypetin, butin, rotterin, chlorophyll A & B, catechin, fisetin, lapachol, juglone, alkannin, alkannan, deoxysantalin, atromentin, awobamin, riboflavin, anthocyanin, lawsone, embilica extract, carajuirin, dracorbohdin, berberine, betanin orcein, xanthone, naphthalene, alfalfa extract, black tea extract, green tea extract, white tea extract and red sandalwood. Preferably, the dye is selected from natural extracts of non-oxidised logwood extract, oxidised logwood extract, containing brazilin, haematin, haematoxylin and brazilin compounds and their mesomeric forms, stereoisomers, acid addition or cosmetically-based addition salts thereof acceptable, as well as hydrates. Further, the dye could be any one or more selected from plant extracts or concentrates of *Haematoxylon campechianum, Haematoxylon brasiletto, Caesalpinia echinata, Caesalpinia sappan, Caesalpinia spinose, Caesalpina brasihensis, Rubia cordifoha, Indigofera tinctora, Lawsonia* sp, *Terminalia chebula* and *Curcuma* sp.

Furthermore, the mordanting agent is selected from inorganic metal salts including, but not limited to Ferrous sulphate, Ferric oxide, Ferric nitrate Zinc sulphate, Zinc nitrate, Zinc Chloride, Zinc Oxide, Copper Sulphate, Copper Nitrate, Copper Chloride, Copper Oxide, Magnesium Sulphate, Magnesium Nitrate, Magnesium Chloride, Magnesium Oxide, Magnesium carbonate, Sodium Chloride, Sodium bicarbonate, Sodium Carbonate, Cobalt Nitrate, Tin Chloride, Barium Chloride, Lead Nitrate, Potassium tellurate, ferrous gluconate.

In an optional embodiment, the composition of the present invention further contains hair cleaning agents selected from sodium lauryl sulfate, sodium laureth sulfate, polyoxyethylene derivatives, decyl glucoside, and lauryl glucoside.

In another optional embodiment, the composition of the present invention may also contain a thickener selected from xanthan gum, quarternized guar and cellulosic gums that provide additional hair smoothing and conditioning effect as compared to traditional thickeners.

In yet another optional embodiment, the composition of the present invention may also include conditioning and colour protective agents like polyquaternium 113, polyquaternium 80, acrylamide copolymer, microbial protein lysates, hydolysable proteins. The current invention also uses shine promoting ingredients like glucam p-20, fancorsil and medaquat HQ-7. The conditioning agent further provides smooth texture and slip feel to hair.

In one more optional embodiment, the natural hair colour composition additionally comprising a cuticle opening inorganic/organic base with subsequent mordant application. It also involves concentrated dye application over the initial two applications. It also states acceptable carriers involving aliphatic and aromatic alcohols, emulsifiers selected from anyone or more of anionic, cationic, non-ionic and amphoteric surfactants, colour protective ingredients, shine and also comprises suitable hair benefiting agents and soothing materials.

In an embodiment, the present invention there is provides a hair colouring product comprising of;
  (a) a basic salt selected from oxides, carbonates, silicates, bicarbonates and carboxyl amine compounds and a concentrated dye selected from, but not limited to non-oxidised logwood extract, oxidised logwood extract, alizarin, pupurin, catechin, napthaquinione, tannins, gallic acid, indigo, indigocaramine, rubiethyric acid, purpuroxanthin, rubiadin, morindanigrin, munjistin, morindadiol, carotene, crocentin, bixin, canthaxanthin, lycopene, capsanthin, apocarotenal, xanthophyll, curcumin, morin, malclurin, luteolin, apigenin, fukugetin, datiscetin, kaempferol, rhamnocitrin, rhamnethinand allied polyhrdroxy compounds.

(b) a mordant selected from, but not limited to ferrous sulphate, ferrous chloride, ferric chloride, ferrous oxide, magnesium carbonate, manganese sulphate, manganese gluconate, zinc sulphate, zinc chloride, zinc nitrate, zinc oxide, potassium tellurate In another embodiment, the composition can be a two-parts, whereby the first part contains the basic essential ingredients, namely, (a) one or more inorganic/organic base and one or more dye, plant dye, concentrated plant dye and the second part contains hair conditioning and colour protective ingredients (b) one or more inorganic metal salt based mordanting agent.

According to yet another embodiment of the present invention, the said hair colour composition additionally comprising a cuticle opening inorganic/organic base with subsequent mordant application. It also involves concentrated dye application over the initial two applications. It also states acceptable carriers involving aliphatic and aromatic alcohols, emulsifiers selected from anyone or more of anionic, cationic, non-ionic and amphoteric surfactants, colour protective ingredients, shine enhancing agents and also comprises suitable hair benefiting agents and soothing materials.

The composition of the present invention can be made available in various physical forms including powders, creams, lotions, sprays, gel. The present invention includes one or more dispersible thickeners or polymers, like carboxymethyl cellulose, guar gum, xanthan gum, agar agar, hydroxyl ethyl cellulose, methyl ethyl cellulose, acrylamide copolymer, quarternized polymers which forms a stable uniform gel. Alternatively, the natural colour can be formulated as a reconstitutable powder, which is a cost-effective product.

In one more embodiment, the invention provides a method of colouring the hair involving said hair colouring composition comprising the steps of:
a. providing an aqueous and, or alcoholic solution of said inorganic/organic base salts along with cellulosic gums with hair cuticle opening effect and applying said dye molecule on the hair in solid and/or in solution form favouring complex formation on the surface or within the hair for effective colouration of the hair through generation of safe modified base colour and/or safe base colour of the dye/plant.
b. providing an aqueous and/or alcoholic solution of the said inorganic metal salt based mordanting agent with or without hair benefiting/conditioning agents on hair, In yet another embodiment of the present invention there is provided a method of colouring the hair involving hair colouring composition comprising the steps of:
a. mixing of the inorganic/organic base salt-based cuticle swelling/opening agents and concentrated dyes/extract containing hair texture benefitting compounds in water and applying the mixture to hair/keratin fibre favouring effective colouration of keratinous fibres in variety of shades under ambient temperature conditions.
b. mixing of the inorganic metal salt based mordanting agent with or without hair benefiting/conditioning agents with or without hair benefiting/conditioning agents in water to achieve uniform consistency, and Yet another preferred embodiment of the present invention provides a composition for dyeing keratin fibres wherein the metal ion solution pH is the natural intrinsic pH of the mordant solution under which it effectively complexes with the dye to yield different insoluble metal ion-dye complex delivering different colours.

Advantageously, the delivery of variants of base colour shade and/or base colour by the composition of the present invention could be thus readily achieved in a three consequent under ambient temperature conditions within time ranging from 30 minutes to 120 minutes, based the requirement of the shade intensity. This invention eliminates the staining and poor colour delivery obtained by prior inventions.

EXAMPLES

Example I:

The experiment protocol is based on conventional methodology for the generation of modified colour and/or base colour shades of the dyes involving one or more basic salts and at least one or more inorganic metal salt based mordanting agent and subsequent combination with dye/plant dye/concentrated plant dye and the results are summarized in the following;

Formulation:

TABLE

Formulation of Natural plant extracts and base salts.

| Composition A: | I (%w/w) | II (%w/w) |
|---|---|---|
| Non oxidised logwood extract | 1.00 | 0.75 |
| Oxidised logwood extract | 1.00 | 0.75 |
| Lawsone extract | 0.75 | 0.25 |
| *Rubia cordifolia* (Maddar extract) | 1.00 | 1.00 |
| Benzyl alcohol | 1.00 | 1.00 |
| 1, 2-Propanol | 1.00 | 1.00 |
| Manganese chloride tetrahydrate | 0.01 | 0.01 |
| Silica | 1.00 | 1.00 |
| Guar gum | 0.50 | 0.50 |
| Polyquat guar 113 | 0.25 | 0.25 |
| Polyquaternium 113 | 1.00 | 1.00 |
| Sodium bicarbonate | 5.00 | 2.50 |
| Water | Q.S. | Q.S. |

Composition A is mixed properly with warm water (50-60° C.) to form gel and applied on the hair tress with more than 40-50% of greys. The ratio of application was 1 g of formulation for 1 g of hair and post application on hair it was left for 45 mins at ambient conditions.

The hair lock can be kept covered for a period of 30 minutes to 120 minutes as per the required shade intensity.

| Composition B: | I |
|---|---|
| Ferrous Sulfate | 2.0 |
| Guar gum | 1.0 |
| Water | Q.S. |

Composition B is then applied over the previously applied composition A at the bath ratio of 1 g formulation for 1 g of hair. The composition was allowed to stand for 10 minutes at ambient conditions.

From the above trials, it was observed that non-oxidised logwood extract which shows a red/pink shade in experimental conditions, also generates different colour shades simply upon selective combination with specific inorganic metal salt based mordanting agents in the absence of any pH controlling agent or oxidizing agent.

It is further observed that Iron salts reacted with non-oxidised logwood extract produce the black/brown shade, Zinc salts react with to generate burgundy shade, copper salts react with non-oxidised logwood extract to yield the brown shade, salts of magnesium reacted with to yield yellow shades, Zinc salts reacted with non-oxidised logwood extract to generate violet shades, magnesium salts and sodium salts also reacted with to result in dark violet/ violet shades thus displaying a broad colour variance in the absence of any pH controlling agent and oxidizing agent.

Example II: The Effect Of pH Controlling Agent On The Colour Of Inorganic/Organic Base-Inorganic Metal Mordant-Dye Complex:

TABLE 2

Effect of pH on colour delivery

| pH of dye | Mordant | Colour |
|---|---|---|
| 3.15-3.30 | FeSO$_4$ | Dark greyish black/soft black with brown tinge |
| 4.00-4.10 | FeSO$_4$ | Dark greyish black with slight blue tinge |
| 5.00-5.10 | FeSO$_4$ | Dark greyish black with blue tinge |
| 7.00-7.15 | FeSO$_4$ | Dark bluish black |

It is noted from Table 2 the combination of dye mordant when the pH of dye ranges of 3-7 gives a range of colour. Blue colour on hair increases with increase in pH while the browner colour with lawsone domination prevails at acidic pH.

Therefore, the intrinsic pH of dyes mixture was also adjusted with external acidic agent like citric acid and aqua acid to desired similar level of 4.0-5.5 to explore the reasons for wide colour variance that may be contributed by specific inorganic metal salt based mordanting agent. The dye uptake and shade direction are summarized as follows:

TABLE 3

Evaluation of mordants:

| Sr. no | Metal mordants | Dye composition | Colour delivery |
|---|---|---|---|
| 1 | Ferrous Sulfate | Non-oxidised logwood extract, madder, Lawsone | Dark greyish black |
| 2 | Ferrous gluconate | Non-oxidised logwood extract, madder, Lawsone | Greyish black |
| 3 | Ferric ammonium citrate | Non-oxidised logwood extract, madder, Lawsone | Brownish grey |
| 4 | Copper sulfate | Non-oxidised logwood extract, madder, Lawsone | Dark grey |
| 5 | Aluminium potassium sulfate | Non-oxidised logwood extract, madder, Lawsone | Grey with lavender tinge |

The above table clearly illustrates that the inorganic ferrous metal salt based mordanting agents provides for superior colour.

Use of hair benefiting agents:

| Sr. no | Compounds | % w/w | Performance |
|---|---|---|---|
| 1 | Polyquaternium-113 (V) | 1.0 | Dark colouration, good feel on hair |
| 2 | Quarternized guar (VIII) | 0.25 | Good colour and gel stability |

Colorimetric Results:

Hair coloring was visually assessed and read with the Minolta spectrocolorimeter (CM3600d, D65 illuminant, 10° angle, SCI values) for L*, a*, b* colorimetric measurements.

In this system L* a* b*, L* represents the intensity of the colour, a* indicates the green/red colour axis and b* the blue yellow axis. The lower the value of L, the darker or more intense the colour. The higher the value of a* the higher the shade is red and the higher the value of b* the hue is yellow.

L*, a* and b* represent the values measured after staining of natural hair/permed at 90% white and L*, a* and b* represent the measured values of natural/permed hair at 90% untreated.

The colour is very resistant to washing and light.

Hair colouring was visually assessed and read with the Minolta spectrocolorimeter (CM3600d, D65 illuminant, 10° angle, SCI values) for L* , a* , b* colorimetric measurements.

The colour is very resistant to washing and light.

TABLE 4

L*a*b* observations for II, IV, V, VI

| Parameters | II | IV | V | VI |
|---|---|---|---|---|
| L* | 13.907 | 16.08 | 13.51 | 14.25 |
| a* | 0.92 | 0.76 | 0.65 | 0.80 |
| b* | −3.747 | −3.193 | −3.02 | −4.56 |
| Colour | Dark | Moderate | Dark | Faint |

We claim:

1. A two-part natural colour composition for dyeing keratinous fibres, including natural human hair, wherein the natural colour composition comprises:
   a) a first part configured to be applied to hair, comprising at least one compound selected from the group consisting of basic salts, organic bases, organic swelling agents; and a natural dye; and
   b) a second part configured to be applied to hair subsequent to application of the first part, comprising an inorganic metal salt based mordanting agent,
      wherein, the natural colour composition exhibits excellent colour coverage and wash off resistance.

2. The two-part natural colour composition as claimed in claim 1, further comprising a hair cleaning agent selected from lauryl sulfate, sodium laureth sulfate, polyoxyethylene derivatives, decyl glucoside, and lauryl glucoside.

3. The two-part natural colour composition as claimed in claim 1, further comprising a thickener selected from xanthan gum, quarternized guar and cellulosic gums in the form of gel.

4. The two-part natural colour composition as claimed in claim 1, further comprising:
   a conditioning and a colour protective agent selected from the group consisting of polyquaternium 113, polyquaternium 80, acrylamide copolymer, microbial protein lysates, hydolysable proteins; and
   a hair shine promoting ingredient selected from the group consisting of a propoxylated methyl glucose ether, fancorsil, and mixtures thereof.

5. The two-part natural colour composition as claimed claim 1, wherein the basic salt is selected from the group consisting of organic and inorganic oxides, carbonates, silicates, and bicarbonates.

6. The two-part natural colour composition as claimed in claim 5, wherein the basic salt is an alkali or alkaline earth carbonate.

7. The two-part natural colour composition as claimed in claim 1, wherein the mordanting agent is selected from the group consisting of Ferrous Sulfate, Ferrous Chloride, Ferric Chloride, Ferrous Oxide, Magnesium Carbonate, Manganese Sulfate, Manganese Gluconate, Zinc Sulphate, Zinc Chloride, Zinc Nitrate, Zinc Oxide, Copper Sulphate, Copper Nitrate, Copper Chloride, Copper Oxide, Magnesium Sulphate, Magnesium Nitrate, Magnesium Chloride, Magnesium Oxide, Magnesium carbonate, Sodium Chloride, Sodium bicarbonate, Sodium Carbonate, Cobalt Nitrate, Tin Chloride, Barium Chloride, Lead Nitrate, potassium tellurate, ferrous gluconate and mixtures thereof.

8. The two-part natural colour composition as claimed in claim 1, wherein the dye is selected from the group consisting of a non-oxidised logwood extract, an oxidised logwood extract, tannins, Benzoquinones, naphthoquinones, anthroquinones, carotenoids, indigo, indigo carmine, rubiethyric acid, purpuroxanthin, rubiadin, morindanigrin, munjistin, morindadiol, carotene, crocentin, bixin, canthaxanthin, lycopene, capsanthin, apocarotenal, xanthophyll, curcumin, morin, malclurin, luteolin, apigenin, fukugetin, datiscetin, kaempferol, rhamnocitrin, rhamnethin, zanthorhamnin, isorhamnetin, rharmazin, quercetin, rutin, gossypetin, butin, rotterin, chlorophyll A & B, catechin, fisetin, lapachol, juglone, alkannin, alkannan, deoxysantalin, atromentin, awobamin, riboflavin, anthocyanin, lawsone, embilica extract, carajuirin, dracorbohdin, berberine, betanin orcein, xanthone, naphthalene, alfalfa extract, black tea extract, green tea extract, white tea extract, red sandalwood, and mixtures thereof.

9. The two-part natural colour composition as claimed in claim 1, wherein the dye is selected from the group consisting of plant extracts of *Haematoxylon campechianum, Haematoxylon brasiletto, Caesalpinia echinata, Caesalpinia sappan, Caesalpinia spinose, Caesalpina brasiliensis, Rubia cordifolia, Indigofera tinctora, Lawsonia* sp, *Terminaha chebula*, and mixtures thereof.

10. The two-part natural colour composition as claimed in claim 1, wherein the natural hair composition further comprises a penetration aiding agent selected from the group consisting of organic ethers, aliphatic alcohols, aromatic/polyhydric alcohols and aldehydes, organic acids and oxones.

11. The two-part natural colour composition as claimed in claim 1, wherein the natural colour composition comprises:
   a) a basic salt in range of 0.5% to 8% by weight and a natural dye in range of 0.1% to 20% by weight.
   b) an inorganic metal salt based mordanting agent in range of 0.01% to 10% by weight.

12. The two-part natural colour composition as claimed in claim 1, wherein the natural colour composition exhibits wash-off resistance for 10 or more washes.

13. The two-part natural colour composition as claimed in claim 1, wherein the natural dye is:
   a logwood extract; or
   a mixture of a logwood extract and at least one of a henna extract, an indigo extract, and a madder extract.

14. The two-part natural colour composition as claimed in claim 10, wherein the penetration aiding agent is lactic acid or benzyl alcohol.

15. A two-part natural colour composition containing two parts, wherein:
   a) a first part contains a natural dye comprising a logwood extract, alone or in combination with at least one of a henna extract, an indigo extract, and a madder extract; and at least one compound selected from the group consisting of basic salts, organic bases, and organic swelling agents; and
   b) a second part contains a metal salt based mordanting agent; wherein:
      the first part is configured to be applied to hair; and
      the second part is configured to be applied after the first part so as to modify a hair color produced by the natural dye.

16. The two-part natural colour composition as claimed in claim 15, wherein the basic salts are selected from the group consisting of organic and inorganic oxides, carbonates, silicates, bicarbonates and carboxyl amine compounds.

17. A method for applying a two-part natural hair colour composition to hair, wherein the two-part natural hair colour composition comprises:
   a first part comprising an aqueous or alcoholic solution of dye and at least one compound selected from the group consisting of basic salts, organic bases, and organic swelling agents;
      wherein the dye comprises a logwood extract, alone or in combination with at least one of a henna extract, an indigo extract, and a madder extract; and
   a second part comprising an aqueous or alcoholic solution of a metal salt based mordanting agent;
   wherein the method comprises:
      a) applying the first part of the two-part natural hair colour composition to the hair;
      b) applying the second part of the two-part natural hair colour composition to the hair 30 minutes to 120 minutes after application of the first part of the two-part natural hair colour composition; and
      c) allowing the mordanting agent in the second part of the two-part natural hair colour composition to form a color-modifying complex with the dye in the first part of the two-part natural hair colour composition.

* * * * *